(12) United States Patent
Sauer et al.

(10) Patent No.: US 10,531,881 B2
(45) Date of Patent: Jan. 14, 2020

(54) TARGET APPARATUS FOR ALIGNING A SURGICAL DRILLING INSTRUMENT

(71) Applicant: KARL STORZ GmbH & Co. KG, Tuttlingen (DE)

(72) Inventors: Michael Sauer, Tuttlingen (DE); Felix Michael Teufel, Tuttlingen (DE); Thomas Weishaupt, Sigmaringen (DE)

(73) Assignee: KARL STORZ SE & Co. KG, Tuttlingen (DE)

( * ) Notice: Subject to any disclaimer, the term of this patent is extended or adjusted under 35 U.S.C. 154(b) by 506 days.

(21) Appl. No.: 15/446,360

(22) Filed: Mar. 1, 2017

(65) Prior Publication Data

US 2017/0252048 A1  Sep. 7, 2017

(30) Foreign Application Priority Data

Mar. 1, 2016 (DE) .................. 10 2016 103 642

(51) Int. Cl.
*A61B 17/17* (2006.01)
*A61B 17/00* (2006.01)

(52) U.S. Cl.
CPC ...... *A61B 17/1714* (2013.01); *A61B 17/1764* (2013.01); *A61B 2017/00862* (2013.01)

(58) Field of Classification Search
CPC ........................... A61B 17/17; A61B 17/1764
See application file for complete search history.

(56) References Cited

U.S. PATENT DOCUMENTS 5,163,940 A * 11/1992 Bourque ............ A61B 17/1714
606/103
6,918,916 B2   7/2005 Göbel et al.
7,842,042 B2   11/2010 Reay-Young et al.
8,690,885 B2 *  4/2014 Smith ................ A61B 17/1714
606/96
8,801,717 B2   8/2014 Herdrich et al.
9,005,212 B2 *  4/2015 Berberich .......... A61B 17/1714
606/96
9,814,508 B2 * 11/2017 Volpi ................. A61B 17/1714
2012/0109136 A1  5/2012 Bourque et al.
2012/0197259 A1  8/2012 Smith

FOREIGN PATENT DOCUMENTS

| DE | 101 46 452 A1 | 4/2003 |
| DE | 10 2010 024 259 A1 | 3/2012 |
| DE | 10 2005 046 299 B4 | 3/2013 |
| FR | 2 911 264 A1 | 7/2008 |
| WO | WO 2006/125009 A2 | 11/2006 |

* cited by examiner

*Primary Examiner* — Anu Ramana
(74) *Attorney, Agent, or Firm* — Muncy, Geissler, Olds & Lowe, P.C.

(57) ABSTRACT

A target apparatus for aligning a surgical drilling instrument that includes a pointer mechanism for arranging at a location on a bone where a drilled hole that is to be formed is intended to emerge, a guide mechanism for guiding the surgical drilling instrument, and an adjustable connection mechanism with a first end, which is connected to the guide mechanism, and a second end, which is connected to the pointer mechanism. The adjustable connection mechanism comprises a first component, a second component and a locking mechanism. The second component is movable relative to the first component along a predetermined path. The first component is elastically deformable by the locking mechanism such that the second component can be locked relative to the first component by clamping.

15 Claims, 2 Drawing Sheets

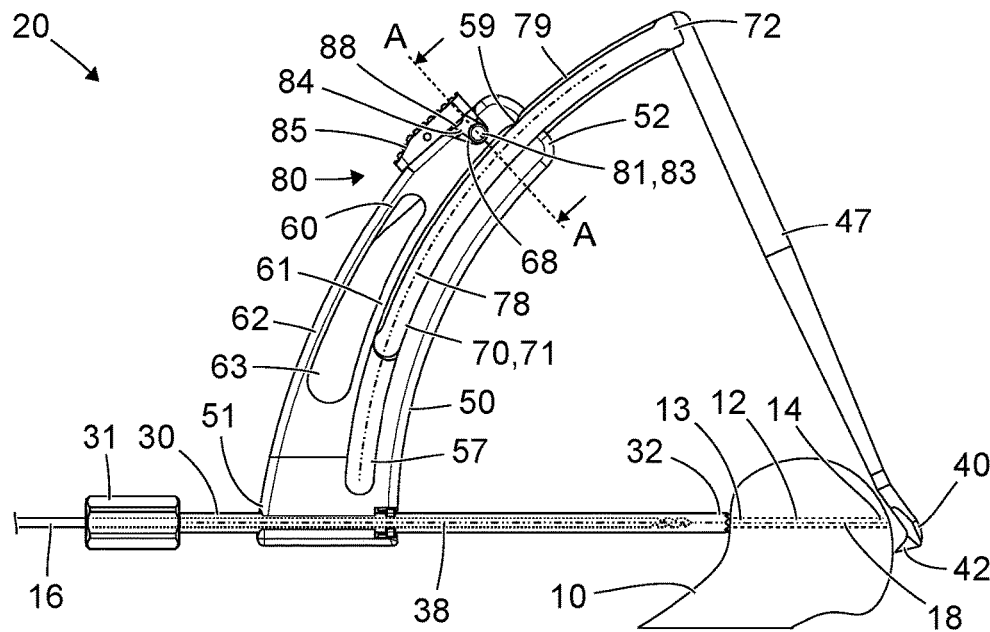
Fig. 1
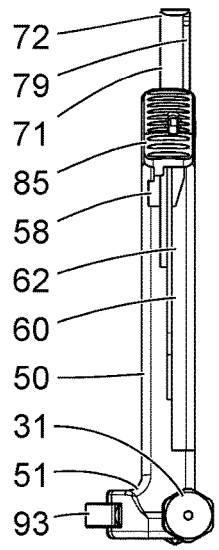
Fig. 2
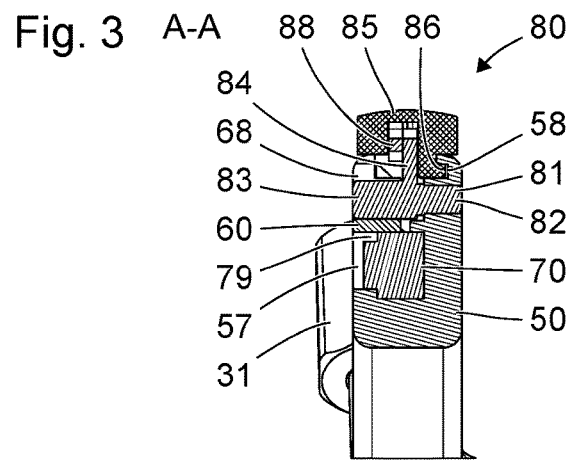
Fig. 3 A-A

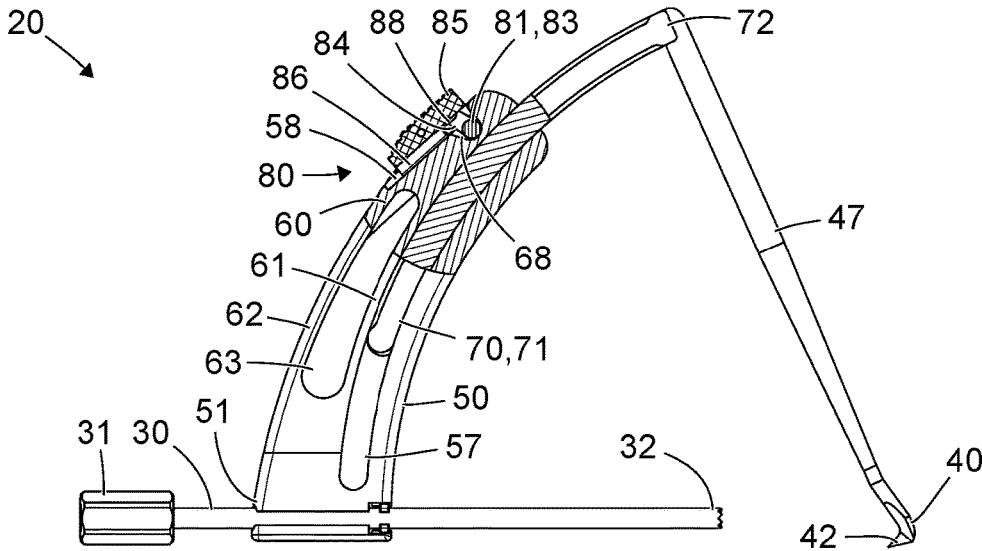
Fig. 4
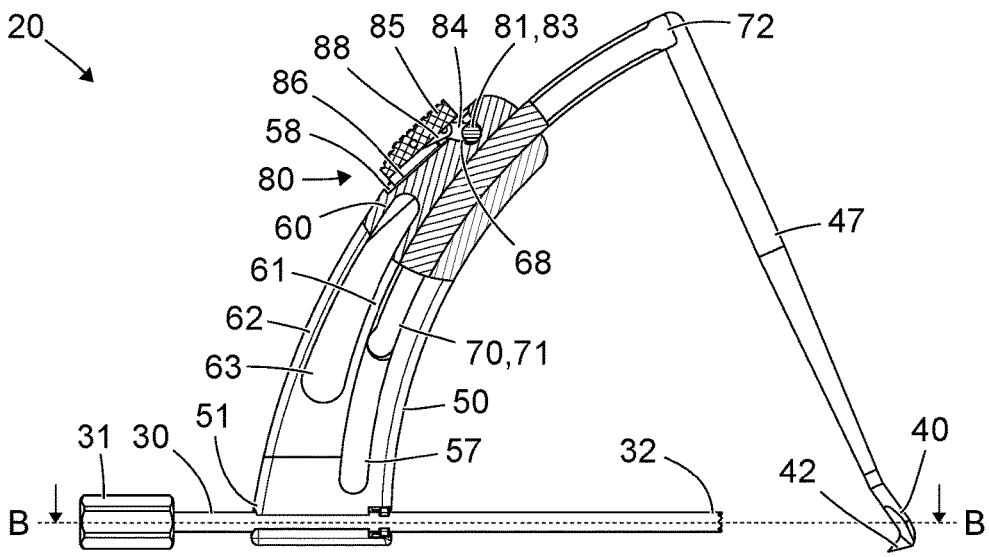
Fig. 5
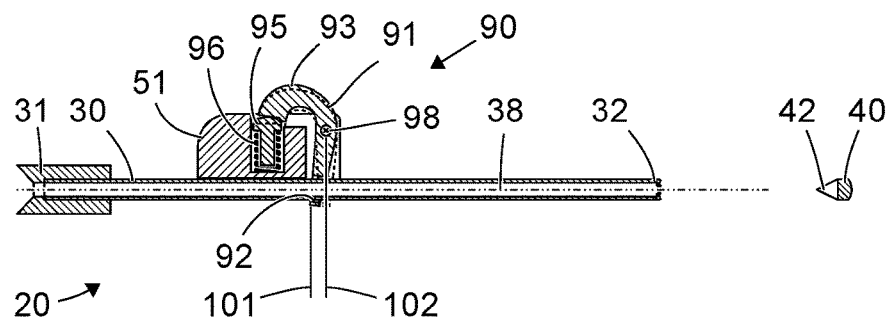
Fig. 6  A-A

TARGET APPARATUS FOR ALIGNING A SURGICAL DRILLING INSTRUMENT

This nonprovisional application claims priority under 35 U.S.C. § 119(a) to German Patent Application No. 10 2016 103 642.0, which was filed in Germany on Mar. 1, 2016, and which is herein incorporated by reference.

BACKGROUND OF THE INVENTION

Field of the Invention

The present invention relates to a target apparatus for aligning a surgical drilling instrument, in particular for forming a drilled hole in the tibia in order to repair a cruciate ligament rupture.

Description of the Background Art

To secure a replacement tendon to a bone, a hole is in particular drilled through the latter. The correct positioning of both ends of the drill channel, in particular also of the outlet opening of the drill channel, is important. For this purpose, a series of target apparatuses were developed which, when used as intended, ensure a correct positioning and orientation of the drilled hole.

DE 101 46 452 A1, which corresponds to U.S. Pat. No. 6,918,916, describes a target apparatus for positioning a drilling tool. An arc-shaped guide arm of the target apparatus can be inserted into an arc-shaped guide path and can be secured there by means of a tensioning cam. A drilling tool can be moved in a receiving seat, wherein a detent permits a movement only in one direction.

DE 10 2005 046 299 B1 describes an aiming appliance with an axially movable aiming tube for guiding a drilling tool. A guide limb is guided in a circular-arc-shaped slit and can be fixed by means of a locking screw. The axially movable aiming tube can be fixed by clamping with the aid of a union nut and two corresponding conical surfaces.

WO 2006/125009 A2, which corresponds to U.S. Pat. No. 7,842,042, describes a device for producing convergent drilled holes. The device comprises a guide arm component and two guiding mechanisms for the alignment of guide pins. The guide arm component and the guiding mechanisms are movable along the guide arc component and can be fixed by means of screws.

DE 10 2010 024 259 A1, which corresponds to U.S. Pat. No. 8,801,717, describes a surgical guiding appliance for cruciate ligament reconstruction. A receiving seat for a sleeve for guiding a drilling wire is movable along an arc-shaped guide arm and can be fixed by clamping with the aid of a clamping lever. The receiving seat has a laterally open groove in which the arc-shaped guide arm is fitted and from which the arc-shaped guide arm can be removed sideways.

US 2012/0109136 A1 describes a guide mechanism for aligning a guide wire. A handle has a curved slit, in which a curved arm is movable and can be locked by a releasable locking mechanism.

U.S. Pat. No. 8,690,885 B2 describes an aiming appliance. The aiming appliance has a handle with an arc-shaped slit. An arc-shaped portion of an arm of the aiming appliance is guided in the slit and can be fixed by means of a fixing stud.

SUMMARY OF THE INVENTION

It is therefore an object of the present invention to provide an improved target apparatus for aligning a surgical drilling instrument.

In an exemplary embodiment, a target apparatus is provided in which a guide mechanism for guiding a surgical drilling instrument and a pointer mechanism are connected to each other by two components movable relative to each other, for locking the two components, one of the two components can be elastically deformed by a locking mechanism in order to obtain clamping or a friction-fit connection between the two components. The locking is thus not effected by direct clamping or friction-fit connection between a screw or an eccentric on one component and an opposite surface on the other component. Instead, the locking mechanism deforms one of the components elastically, in such a way that the latter is pressed against the other component in such a way that clamping or a friction-fit connection is produced.

A target apparatus for aligning a surgical drilling instrument comprises a pointer mechanism for arranging at a location on a bone where a drilled hole that is to be formed is intended to emerge, a guide mechanism for guiding the surgical drilling instrument, and an adjustable connection mechanism with a first end, which is connected to the guide mechanism, and a second end, which is connected to the pointer mechanism, wherein the adjustable connection mechanism comprises a first component, a second component and a locking mechanism, wherein the second component is movable relative to the first component along a predetermined path, and wherein the first component is elastically deformable by the locking mechanism in such a way that the second component can be locked relative to the first component by clamping.

The target apparatus is in particular provided and designed to assist in the formation of a drilled hole in the tibia for repair of a cruciate ligament rupture. The pointer mechanism is provided and designed to simplify a visual and/or tactile test of the positioning of the pointer mechanism. The pointer mechanism comprises in particular an aiming hook, one or more tips and/or one or more other mechanisms that simplify a positioning of the pointer mechanism. Moreover, the pointer mechanism can be designed such that it can temporarily be held with force-fit and/or form-fit engagement on a surface of a bone, and slipping or an inadvertent change of its position can be prevented.

The guide mechanism comprises in particular one or more tubes or sleeves for guiding the surgical drilling instrument. The guide mechanism has in particular a channel, of which the cross section is adapted to the cross section of the surgical drilling instrument, for which the target apparatus is provided, in such a way that the surgical drilling instrument is guided with little play and little friction in the guide mechanism.

The adjustable connection mechanism also has in particular the function of a handle by means of which the target apparatus can be held and guided with one hand. In particular, the first component is designed as a handle component. The locking mechanism or at least an operating element or mechanical command initiator of the locking mechanism is arranged in particular on the first component. Alternatively, the locking mechanism or at least an operating element of the locking mechanism can be arranged on the second component.

The first component is in particular connected rigidly or movably to the guide mechanism. In particular, the guide mechanism is movable relative to the first component along a predetermined path. The predetermined path along which the guide mechanism is movable relative to the first component is in particular straight and parallel to the path or identical to the predetermined path along which a surgical drilling instrument can be guided by the guide mechanism. The second component is in particular rigidly connected to the pointer mechanism. Alternatively, the first component is mechanically connected to the pointer mechanism and the second component to the guide mechanism.

The predetermined path along which the second component is movable relative to the first component is in particular defined by a form fit with little play and little friction. The predetermined path along which the second component is movable relative to the first component has in particular the shape of an arc of a circle. The centre point of the arc of the circle lies in particular on the pointer mechanism, more specifically at a location on the pointer mechanism that is intended to be arranged at a location on a surface of a bone where a drilled hole to be formed is intended to emerge. The centre point of the arc of the circle lies in particular on an axis of symmetry of the guide mechanism or on an axis of symmetry of a surgical drilling instrument inserted as intended into the guide mechanism. The connection mechanism can permit a variation and adjustment of the orientation of the pointer mechanism relative to the guide mechanism without changing the position of the location, indicated by the pointer mechanism, relative to the guide mechanism.

Compared to a screw or another locking mechanism that acts directly on the second component and establishes a friction-fit connection with the latter, locking obtained by elastic deformation of the first component has a number of advantages. In particular, it is possible to prevent damage to a surface of the second component by the locking mechanism. Moreover, the second component does not need to have a surface area suitable for direct contact of the locking mechanism. Since the locking mechanism does not act directly on the second component, and instead merely elastically deforms the first component, it is also possible to prevent an inadvertent movement of the second component relative to the first component during the locking. Conversely, forces that load the locking, or movements of the second component relative to the first component caused by play, cannot lead or cannot easily lead to release of the locking mechanism.

In a target apparatus as described here, the first component has in particular a recess in which the second component is guided movably along the predetermined path, wherein the first component is elastically deformable, in the area of the recess, by the locking mechanism in such a way that the second component can be locked in the recess by clamping.

The recess in the first component is in particular a groove with a cross section that is constant or substantially constant along the predetermined path. The groove has in particular the shape of an arc of a circle. The contour of the cross section of the groove is in particular C-shaped or substantially C-shaped with curved and/or straight portions.

The cross section of the groove in particular is deformable by the locking mechanism. The locking mechanism is in particular arranged and designed such that it deforms the cross section of the groove or of the other recess at a location where, during the intended use, the second component is always arranged inside the groove or the other recess.

Alternatively or in addition, the second component can have a groove or another recess in which the first component is guided movably along the predetermined path. In this case, the cross section of the first component can in particular be enlarged elastically by the locking mechanism in such a way that the first component can be locked in the recess by clamping. The locking mechanism is in particular arranged and designed such that it deforms the cross section of the first component at a location which, during the intended use, is always arranged inside the groove or the other recess.

A recess, in particular a groove, with a non-circular cross section can be easy to produce and, moreover, can permit reliable guiding with little play and little friction.

In a target apparatus as described here, the first component has in particular an elastic portion which forms a part of the surface of the recess.

The elastic portion forms in particular a part of an inner surface of the recess, which part lies opposite another part of the inner surface of the recess, for example lies opposite this and in parallel.

The first component is in particular designed such that the second component is held with form-fit engagement on the first component even in the absence of the elastic portion, for example prior to assembly or after disassembly. For example, a recess in the first component and the second component itself, if it is to be arranged in the recess, each have a substantially rectangular cross section. In this case, the first component and the second component are in particular designed such that, setting play aside, they touch each other on each of the four sides of the cross sections.

In a target apparatus as described here, the elastic portion of the first component is formed in particular by a structural element that is produced separately and thereafter attached.

The separately produced structural element forming the elastic portion of the first component is mechanically rigidly connected to the one or more other structural elements, which form the first component, by a screw connection with one, two or more screws. Alternatively or in addition, the structural element forming the elastic portion of the first component can be mechanically rigidly connected to the one or more other structural elements, which form the first component, in another way by form-fit engagement and/or by adhesive bonding, by a soldered or welded connection, or another cohesively bonded connection.

The formation of the elastic portion from a separately produced structural element allows different materials to be used. In particular, the separately produced structural element forming the elastic portion can have a plastic or a metal, the surface properties of which promote frictional locking, and/or which has a higher elasticity.

In a target apparatus as described here, the elastic portion has in particular a tongue-shaped design and extends along the recess.

The elastic portion has in particular a first end which is connected rigidly (and optionally in one piece) to the one or more other structural elements of the first component. The second end of the elastic portion is movable relative to the first end, within a predetermined range, by means of the locking mechanism and on account of the elastic properties of the elastic portion.

In a target apparatus as described here, the elastic portion has in particular two elastically deformable beam-shaped areas.

The two elastically deformable beam-shaped areas can each be straight or curved in parts. In particular, the two elastically deformable beam-shaped areas are each shaped as an arc of a circle or substantially as an arc of a circle. The two elastically deformable beam-shaped areas are in particular arranged substantially parallel to each other. In particular, the two elastically deformable beam-shaped areas enclose an angle that is not greater than 2 degrees or not greater than 5 degrees or not greater than 10 degrees.

The two elastically deformable beam-shaped areas are in particular formed by a recess being made between them. The cross sections of the two elastically deformable beam-shaped areas are each, for example, narrow and elongate, for example rectangular. The dimensions of the elastically deformable beam-shaped areas, in a direction orthogonal to the surface area of the elastic portion intended to bear on the second component, are in particular smaller or much smaller than the other dimensions of the elastically deformable beam-shaped areas. This can result in much greater elasticity of the elastic portion in the direction in which it is deformed by the locking mechanism than in a direction orthogonal thereto.

In a target apparatus as described here, the locking mechanism has in particular an operating element movable along a predetermined path.

The operating element or the mechanical command initiator for controlling the locking mechanism is in particular slidable along a straight path. Especially in one-handed operation or manoeuvring of the target apparatus, a sliding movement of an operating element can be easier than turning a screw or pivoting a lever. In particular, a sliding movement of the operating element is easily possible by means of one finger.

In a target apparatus as described here, the movable operating element is guided in particular in a groove in the first component.

The movable operating element has in particular a web which engages in the groove in the first component. The groove and the web are designed such that the web is guided in the groove with little play and little friction. The web can have a straight or an angled cross section, depending on its arrangement on the movable operating element.

In a target apparatus as described here, the movable operating element has in particular a groove in which a web on the first component is guided.

In a target apparatus as described here, the operating element is held with form-fit engagement in the groove in the first component, in particular by the elastic portion of the first component.

Particularly when the elastic portion is designed as a structural element that is initially separately produced and thereafter attached, the operating element can be held on the first component by the elastic portion. After separation of the elastic portion from the one or more other structural elements of the first component, the operating element can be separated from the first component. This can simplify the cleaning of the whole target apparatus.

In a target apparatus as described here, the locking mechanism comprises in particular an eccentric or a cam on a pivotable structural element.

An eccentric or a cam can convert a torque on the pivotable structural element into a normal force between, on the one hand, a surface of the eccentric or of the cam and, on the other hand, the elastic portion of the first component.

In a target apparatus as described here, the pivotable structural element and a lever are in particular rigidly connected, wherein the lever and the movable operating element are mechanically coupled by means of a connecting rod.

The lever is in particular designed in one piece with the pivotable structural element and with the eccentric or cam. The connecting rod is subjected to thrust particularly when the locking is produced and is subjected to tensile load when the locking is released. The connecting rod couples a linear movement of the operating element to a pivoting movement of the pivotable structural element. Through the choice of the lengths of the lever and of the connecting rod, through the choice of the angle at which the lever is arranged relative to the eccentric or cam on the pivotable structural element, and through the choice of further geometric properties of the pivotable element, of the connecting rod and of the movable operating element, it is possible to achieve a transmission ratio that varies during the production or release of the locking.

In a target apparatus as described here, the pivotable structural element has in particular a tooth which engages in a recess on the movable operating element, or several teeth which engage in a toothed rack on the movable operating element.

This permits a mechanical coupling of a linear movement of the movable operating element and of a pivoting movement of the pivotable structural element, without the need for a connecting rod and with a constant or substantially constant transmission ratio.

In a target apparatus as described here, the second component has in particular a groove in which the first component engages, wherein the groove on the second component ends at the end directed towards the first component such that the second component cannot be separated from the first component.

In particular, a projection on the elastic portion on the first component is provided which engages in the groove in the second component. In this case, the second component can be separated from the first component, if appropriate after disassembly of the elastic portion.

In a target apparatus as described here, the guide mechanism is in particular movable relative to the first end of the adjustable connection mechanism along a predetermined path, wherein a further locking mechanism is provided for locking the guide mechanism, and wherein the further locking mechanism is designed such that a movement of the guide mechanism towards the pointer mechanism is possible at any time within a predetermined range, and a movement of the guide mechanism away from the pointer mechanism is possible only upon actuation of a further operating element.

The predetermined path along which the guide mechanism is movable relative to the first end of the connection mechanism is in particular straight.

By designing the further locking mechanism in such a way that, without actuation of an associated further operating element, a movement of the guide mechanism is possible only towards the pointer mechanism, it is possible for the target apparatus to be arranged on a bone quickly and securely.

In a target apparatus as described here, the further locking mechanism is in particular designed to suppress a movement of the guide mechanism away from the pointer mechanism solely by frictional engagement.

The predetermined path along which the guide mechanism is movable relative to the first end of the connection mechanism is in particular straight. The locking mechanism is designed in particular such that it permits a movement of the guide mechanism towards the pointer mechanism within a predetermined range at any time and permits a movement of the guide mechanism away from the pointer mechanism only upon actuation of an operating element.

Further features, properties and functions of the target apparatus may correspond to those of the other target apparatuses described here.

By designing the locking mechanism for the guide mechanism in such a way that it suppresses a movement of the guide mechanism away from the pointer mechanism solely by frictional or force-fit engagement but permits a movement of the guide mechanism towards the pointer mechanism within a predetermined range and in particular at any time, the target apparatus can be arranged on a bone simply, quickly and securely. The suppression of a movement of the guide mechanism away from the pointer mechanism solely by frictional engagement can permit stepless positioning of the guide mechanism. Stepless positioning is not possible, for example, when the guide mechanism is locked by latched engagement.

In a target apparatus as described here, the further locking mechanism comprises in particular a lever, which is pivotable about a further pivot axis, a friction surface on the lever for bearing on a surface area of the guide mechanism directed away from the further pivot axis, and an elastic mechanism for moving the friction surface away from the pointer mechanism.

The distance of the pointer mechanism from a first plane, which is orthogonal to the predetermined path of the guide mechanism and contains a contact point between the friction surface on the lever and the guide mechanism, is in particular greater than the distance of the pointer mechanism from a second plane, which is orthogonal to the predetermined path of the guide mechanism and contains the further pivot axis of the lever.

In a target apparatus as described here, the further locking mechanism comprises in particular a lever which is pivotable about a further pivot axis, a friction surface on the lever for bearing on a surface area of the guide mechanism directed towards the further pivot axis, and an elastic mechanism for moving the friction surface away from the pointer mechanism.

The distance of the pointer mechanism from a first plane, which is orthogonal to the predetermined path of the guide mechanism and contains a contact point between the friction surface on the lever and the guide mechanism, is in particular smaller than the distance of the pointer mechanism from a second plane, which is orthogonal to the predetermined path of the guide mechanism and contains the further pivot axis of the lever.

To put it simply, either the friction surface bears on the side of the guide mechanism directed away from the pivot axis of the lever at a point which is arranged farther proximally than the pivot axis of the lever, or the friction surface bears on a side of the guide mechanism directed towards the pivot axis of the lever and contacts the guide mechanism at a point which is arranged farther distally than the pivot axis of the lever. In both cases, the guide mechanism can be moved in the distal direction, i.e. towards the target apparatus, since only the frictional force generated by the elastic mechanism between the friction surface and the surface of the guide mechanism has to be overcome. However, if a force oriented in the proximal direction is exerted on the guide mechanism, then, on account of the geometry, the friction between the friction surface and the surface of the guide mechanism and also between the guide mechanism and the first end of the connection mechanism is increased to such an extent that a movement of the guide mechanism in the proximal direction is not possible. Only when the lever is moved manually, such that the friction surface is moved away from the surface of the guide mechanism counter to the restoring force of the elastic mechanism, can the guide mechanism be released and allowed to move in the proximal direction.

Further scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

The present invention will become more fully understood from the detailed description given hereinbelow and the accompanying drawings which are given by way of illustration only, and thus, are not limitive of the present invention, and wherein:

FIG. 1 shows a schematic view of a target apparatus for aligning a surgical drilling instrument;

FIG. 2 shows a further schematic view of the target apparatus from FIG. 1,

FIG. 3 shows a schematic sectional view of the target apparatus from FIGS. 1 and 2;

FIG. 4 shows a further schematic sectional view of the target apparatus from FIGS. 1 to 3;

FIG. 5 shows a further schematic sectional view of the target apparatus from FIGS. 1 to 4; and FIG. 6 shows a further schematic view of a section through the target apparatus from FIGS. 1 to 5.

DETAILED DESCRIPTION

FIG. 1 shows a schematic view of a bone 10 in which a cylindrical drilled hole 12 is to be formed. The drilling tool 16 is partly concealed and therefore indicated by a broken-line contour. The proximal end of the drilling tool 16 lies outside the area shown.

A first end 13 of the drilled hole 12, being the end from which the drilled hole 12 is advanced, can be precisely positioned even when the drilling instrument 16 is guided free-hand. The position of the second end 14 of the drilled hole 12, being the end where the drilling instrument 16 is intended to emerge again from the bone 10 when the drilled hole 12 has been completed, is highly dependent on the direction or orientation of the axis 18 of the drilled hole 12. Therefore, the precision with which the position of the second end 14 of the drilled hole 12 can be determined in advance is, in many applications, unsatisfactory without the use of an aid.

In FIG. 1, the aid for forming the drilled hole 12 is shown as a target apparatus 20 with a guide mechanism 30 for the drilling instrument 16. In the example shown, the guide mechanism 30 of the target apparatus 20 has the form of a straight tube with the longitudinal axis and axis of symmetry 38. The cross section of the cavity of the guide mechanism 30 is adapted to the cross section of the drilling instrument 16 such that the drilling instrument 16 is guided in the guide mechanism 30 with little play and little friction. Optionally, the cross section of the cavity of the guide mechanism 30 and the cross section of the drilling instrument 16 can be designed such that an irrigation liquid can additionally flow through the guide mechanism 30.

In the example shown, a proximal end 31 of the guide mechanism 30 has approximately the form of a cylinder with a regular hexagonal cross section, in order to allow the proximal end 31 of the guide mechanism 30 to be securely gripped and guided manually. In the example shown, a distal end 32 of the guide mechanism 30 has several tips or teeth, which simplify a positioning of the distal end 32 of the guide mechanism 30 on the surface of the bone 10 and can reduce the likelihood of an inadvertent movement of the distal end 32 of the guide mechanism 30 on the surface of the bone 10.

The target apparatus 20 moreover comprises a pointer mechanism 40 with a tip 42. The tip 42 of the pointer mechanism 40 is provided and designed for the tactile locating of surface structures even on a bone 10 surface that is not directly visible to medical personnel since directed away from them. Alternatively or in addition, the tip 42 of the pointer mechanism 40 is provided and designed to prevent any sliding or slipping of the pointer mechanism 40 on the surface of a bone 10 or at least to make such sliding or slipping less likely.

The pointer mechanism 40 is arranged at the end of a shank 47 which, in the example shown, is straight and has a circular cylindrical portion and a conical portion. The pointer mechanism 40 and the shank 47 can be produced in one piece or can be formed by joining together two or more structural elements.

The target apparatus 20 moreover has an adjustable connection mechanism composed of a first component 50 and a second component 70. A first end 51 of the first component 50 is mechanically connected to the guide mechanism 30. FIG. 6 shows that the guide mechanism 30 is movable relative to the first end 51 of the first component 50 in a direction parallel to the longitudinal axis and axis of symmetry 38 of the guide mechanism 30. A second end 52 of the first component 50 is directed towards the shank 47.

A first circular-arc-shaped groove 57 extends from the second end 52 almost to the first end 51 of the first component 50. The likewise substantially circular-arc-shaped second component 70 is arranged in the first groove 57. The curvature and the cross section of the first groove 57 in the first component 50 and the curvature and the cross section of the circular-arc-shaped second component 70 correspond substantially to each other, such that the second component 70 is guided in the first groove 57 with little play and little friction and is movable relative to the first component 50 along a circular-arc-shaped path 78. The circular-arc-shaped path 78 is predefined by the shape of the first groove 57 in the first component 50 and by the shape of the second component 70.

A first end 71 of the second component 70 is arranged in the first groove 57 in the first component 50. In the configuration or situation shown in FIG. 1, a second end 72 of the second component 70 is at a distance from the first component 50. The second end 72 of the second component 70 is connected mechanically rigidly to an end of the shank 47 at a distance from the pointer mechanism 40. During movement of the second component 70 relative to the first component 50 along the circular-arc-shaped path 78, the first end 71 of the second component 70 remains in the first groove 57 in the first component 50. The second end 72 of the second component 70 is located at a modifiable distance from the second end 52 of the first component 50.

The centre point of the circular-arc-shaped path 78, along which the second component 70 is movable relative to the first component 50, lies in particular on or near the longitudinal axis and axis of symmetry 38 of the guide mechanism 30 and close to the pointer mechanism 40. This ensures that, independently of the position of the second component 70 relative to the first component 50, the pointer mechanism 40 marks the position of the second end 14 of the drilled hole 12 that is to be formed.

The second component 70 has a groove 79 in which a projection 59 on the first component 50 engages. The groove 79 does not extend fully along the entire length of the second component 70. The engagement of the projection 59 on the first component in the groove 79 on the second component ensures that the first end 71 of the second component 70 remains in the first groove 57 in the first component 50 and ensures that the second component 70 cannot be removed completely from the groove 57 in the first component 50 and thus separated from the first component 50. The first component 50 and the second component 70 thus form a unit that is modifiable or adjustable but that cannot readily be separated.

The first component 50 has an elastic portion 60. The elastic portion 60 is tongue-shaped and extends substantially parallel to the first groove 57 in the first component 50. The elastic portion 60 comprises in particular a first elastic web 61 and a second elastic web 62. The webs 61, 62 are in particular formed by a recess 63 being produced between the webs 61, 62.

The end of the elastic portion 60 directed towards the first end 51 of the first component 50 is rigidly connected to the rest of the first component 50. The elastic deformability of the webs 61, 62 permits an elastic deformation of the elastic portion 60, within a predetermined range, and a movement of the end of the elastic portion 60 arranged at the second end 52 of the first component 50. In the example shown, the first elastic web 61 and the second elastic web 62 of the elastic portion 60 each have substantially the form of an arcuately curved beam of substantially rectangular cross section.

The dimensions of the cross sections of the elastic webs 61, 62 in a direction orthogonal to the drawing plane of FIG. 1 are greater or much greater than the dimensions of the elastic webs 61, 62 in a direction parallel to the drawing plane of FIG. 1. Therefore, the elastic portion 60, in particular the end thereof directed towards the second end 52 of the first component 50, is much more easily deformable or deflectable in a direction parallel to the drawing plane of FIG. 1, and substantially orthogonal to the path 78, than it is in a direction orthogonal to the drawing plane of FIG. 1.

Apart from the elastic portion 60, the first component 50 is substantially rigid or non-elastic on account of its much greater cross sections and/or on account of a less elastic material.

The elastic portion 60 and the rigid portion of the first component 50 can be produced in one piece and at the same time. Alternatively, the elastic portion 60 can firstly be produced as a separate component and, as is indicated in FIG. 1 by a partition line near the first end 51 of the first component 50 and to the left of the first groove 57, can thereafter be joined to the first component 50. In particular, the elastic portion 60 can be joined to the rest of the first component 50 by screwing and/or by some other form-fit connection, cohesively bonded connection and/or force-fit connection or frictional connection. In this case, the elastic portion 60 can be of another material than the rest of the first component 50, in particular a material of higher elasticity. Alternatively, the elasticity of the elastic portion 60 results exclusively from its geometry, in particular the cross sections of the elastic webs 61, 62.

The elastic portion 60, in particular the first elastic web 61 of the elastic portion 60, forms a part of the inner surface of the first groove 57 in the first component 50. The elastic portion 60 of the first component 50 thus bears on the second component 70 or can bear on the second component 70.

The target apparatus 20 moreover comprises a first locking mechanism 80, by means of which the elastic portion 60 of the first component 50 can be pressed against the second component 70 in order to lock the second component 70 with friction-fit or force-fit engagement in the first groove 57 in the first component 50.

The first locking mechanism 80 comprises a pivotable structural element 81, which is pivotable about an axis orthogonal to the drawing plane of FIG. 1, and of which only an eccentric 83 and a lever 84 can be seen in FIG. 1. The locking mechanism 80 moreover comprises a slide 85 as a first operating element. The slide 85 is movable relative to the first component 50 of the adjustable connection mechanism of the target apparatus 20 along a predetermined straight path parallel to the drawing plane of FIG. 1. A connecting rod 88 is arranged substantially inside a cavity in the slide 85 open to the first component 50 and, consequently, only a small part thereof can be seen in FIG. 1. The connecting rod 88 connects the slide 85 to an end of the lever 84 directed away from the eccentric 83 and from the pivot axis of the pivotable structural element 81. The connecting rod 88 couples a translation movement of the slide 85 with a rotation movement of the pivotable structural element 81, in particular of the lever 84 and of the eccentric 83.

The eccentric 83 is arranged in a notch 68 in the elastic portion 60 of the first component 50. By movement of the slide 85 and by the associated pivoting of the eccentric 83, the elastic portion 60 of the first component 50 can be moved in a direction orthogonal to the path 78 and, in particular, can be pressed against the second component 70. In the situation or configuration shown in FIG. 1, the slide 85 is in particular arranged in a position near the second end 52 of the first component 50, the elastic portion 60 of the first component 50 is pressed against the second component 70, and the second component is thus held in the first groove 57 in the first component 50 by clamping, that is to say by force-fit or friction-fit engagement.

FIG. 2 shows a further schematic view of the target apparatus 20 from FIG. 1. The drawing plane of FIG. 2 is orthogonal to the drawing plane of FIG. 1 and orthogonal or substantially orthogonal to the longitudinal axis and axis of symmetry 38 of the guide mechanism, of which only the proximal end 31 is visible in FIG. 2. In the example shown, the elastic portion 60 of the first component 50 is formed from a structural element which is originally separately produced and then joined to the rest of the first component 50. FIG. 2 also shows an end of a second groove 58 in the first component 50. A web (not visible in FIG. 2) on the slide 85 engages in the second groove 58, such that the slide 85 is held with form-fit engagement on the first component 50 and is movable relative to the component 50 along a predetermined path.

A second operating element 93 of a second locking mechanism, which is not visible in FIG. 2, is arranged at the first end 51 of the first component 50.

FIG. 3 shows a schematic view of a section along the plane A-A, indicated in FIG. 1, orthogonal to the path 78. The section plane A-A of FIG. 3 contains the pivot axis of the aforementioned pivotable structural element 81. The depiction in FIG. 3 is enlarged by comparison with the depictions in FIGS. 1 and 2 so that details can be better seen.

The section plane A-A of FIG. 3 intersects the elastic portion 60 of the first component 50 in the area of the notch 68 (cf. FIG. 1). The cross section of the elastic portion 60 visible in FIG. 3 is therefore small. The cross section of the rest of the first component 50 is substantially L-shaped and comparatively solid, in order to permit rigid and non-elastic guiding of the second component 70 in the first component 50.

The cross section of the groove 57 in the first component 50 and the cross section of the second component 70 are each substantially rectangular. The cross section of the rigid portion of the first component 50 (that is to say without the elastic portion 60) engages around the second component 70 such that, with respect to two orthogonal directions (in FIG. 3: horizontal and vertical), the first component 50 bears on two mutually opposite and parallel surface portions of the second component 70. The second component 70 is thus guided completely in the first component 50 even without consideration of the elastic portion 60.

The pivotable structural element 81 already mentioned in the context of FIG. 1 comprises a shaft or a journal 82, which is mounted with little play in a bore in the rigid portion of the first component 50. Moreover, the pivotable element 81 comprises the aforementioned eccentric 83 which, in the situation or configuration shown in FIGS. 1 to 3, presses the elastic portion 60 against the second component 70 and thereby locks the second component 70 with frictional engagement or force-fit engagement in the first groove 57 in the first component 50. The connecting rod 88 is cut by the section plane A-A of FIG. 3 only at its end directed towards the lever 84 on the pivotable structural element 81.

The aforementioned web 86 (not visible in FIGS. 1 and 2) on the slide 85 has an L-shaped cross section and engages in the second groove 58 in the first component 50, the end of which groove 58 can be seen in FIG. 2.

FIG. 4 shows a further schematic view of the target apparatus 20 from FIGS. 1 to 3. The drawing plane of FIG. 4 corresponds to the drawing plane of FIG. 1. In contrast to FIG. 1, however, the target apparatus 20 is shown in section in the area of the first locking mechanism 80. The situation or configuration shown in FIG. 4 corresponds to the one shown in FIGS. 1 to 3.

An end of the second groove 58, in the first component 50, and the web 86 on the slide 85 are visible in FIG. 4.

FIG. 5 shows a further schematic view of the target apparatus 20 from FIGS. 1 to 4. The nature of the view corresponds to that of FIG. 4. In contrast to FIG. 4, however, the target apparatus 20 is shown in another situation or configuration. Proceeding from the position shown in FIGS. 1 to 4, the slide 85 is moved in the proximal direction, i.e. towards the first end 51 of the first component 50. On account of the coupling of the slide 85 to the lever 84 and to the eccentric 83 by the connecting rod 88, the eccentric 83 is turned anticlockwise in relation to the situation shown in FIGS. 1 to 4. The eccentric 83 therefore exerts less force or no force on the elastic portion 60 of the first component 50, such that the second component 70 is not locked by force-fit or friction-fit engagement but instead can be moved relative to the first component 50 along the path 78 (cf. FIG. 1).

FIG. 6 shows a schematic view of a further section through the target apparatus 20 from FIGS. 1 to 5, along the plane B-B indicated in FIG. 5. The section plane B-B is orthogonal to the drawing planes of FIGS. 1, 2, 4 and 5 and contains the longitudinal axis and axis of symmetry 38 of the guide mechanism 30.

The section plane B-B intersects the second locking mechanism 90, which has already been mentioned in the context of FIG. 2 but is not visible in FIG. 2. The second locking mechanism 90 comprises a substantially L-shaped lever 91, which is pivotable about a pivot axis 98 orthogonal to the section plane B-B of FIG. 6. An end of the lever 91 engages in a fork shape around the guide mechanism 30 and bears with friction surfaces 92 on the side of the guide mechanism 30 directed away from the pivot axis 98. The second limb of the lever 91 forms the operating element 93 (also visible in FIG. 2) and bears on a stamp 95. A helical spring 96 presses the stamp 95 and therefore the lever 91 into the positions shown in FIG. 6. By manual pressure applied to the area of the lever 91 provided as second operating element 93, the lever 91 can be pivoted against the elastic restoring force of the helical spring 96 into a position of which the contours are indicated in FIG. 6 by broken lines.

In the situation shown in FIG. 6, a contact point between the friction surface 92 on the lever 91, on the one hand, and the guide mechanism 30, on the other hand, lies farther proximally (farther to the left in FIG. 6) than the pivot axis 98. More precisely, a first plane 101, which is orthogonal to the longitudinal axis and axis of symmetry 38 of the guide mechanism 30 and contains the contact point between the friction surface 92 on the lever 91 and the guide mechanism 30, is farther away from the distal end 32 of the guide mechanism 30 than a second plane 102, which is parallel to the first plane 101 and contains the pivot axis 98 of the second locking mechanism 90.

As a result of the geometry shown, a proximally oriented force on the guide mechanism 30 causes a clamping of the guide mechanism 30. By frictional or force-fit engagement, the clamping suppresses a movement of the guide mechanism 30 relative to the first end 51 of the first component of the adjustable connection mechanism. The guide mechanism 30 can be moved in the proximal direction only when pressure is exerted at the same time on the area of the lever 91 provided as second operating element 93 and when the latter is pivoted in the direction of the release position indicated by broken lines in FIG. 6.

By contrast, a movement of the guide mechanism 30 in the distal direction relative to the first end 51 of the first component of the adjustable connection mechanism is possible at all times.

To replace the guide mechanism 30 or to dismantle the target apparatus 20, the guide mechanism 30 can be pulled in the proximal direction from the first end 51 of the first component 50. For this purpose, all that has to be done is to exert pressure at the same time on the area of the lever 91 provided as second operating element 93 and to pivot the latter in the direction of the release position indicated by broken lines in FIG. 6.

To further dismantle the target apparatus 20, it is possible, in a next step, to separate the first locking mechanism 80 from the first component 50. In the example shown here, the pivotable structural element 81 and the notch 68 in the elastic portion 60 of the first component 50 are designed such that the pivotable structural element 81 together with the connecting rod 88 and the slide 85 can be separated from the first component 50 by being moved relative to the latter in a direction orthogonal to the drawing planes of FIGS. 1, 4 and 5 and parallel to the drawing planes of FIGS. 2 and 3. The journal 82 of the pivotable structural element 81 is removed from the corresponding bore in the rigid portion of the first component 50 and, at the same time, the L-shaped web 86 on the slide 85 is removed from the second groove 58 on the first component 50. The direction of movement is to the right with respect to FIG. 2 and to the left with respect to FIG. 3.

The lever on the pivotable structural element 81 and the notch 68 in the elastic portion 60 of the first component 50 are in particular designed such that the described movement of the pivotable structural element 81 relative to the first component 50 is possible only when the pivotable structural element 81 adopts a predetermined angle position, for example the one shown in FIGS. 1 and 4. This angle position can be identified by markings on the first component 50 and on the slide 85. The lever on the pivotable structural element 81 and the notch 68 in the elastic portion 60 of the first component 50 are in particular designed such that the described movement of the pivotable structural element 81 is possible only in a single angle position or within a small or very small range of angle positions. In all other angle positions, particularly in the two extreme or end positions, the lever 84 on the pivotable structural element 81 is prevented, by form-fit engagement of the elastic portion 60 of the first component 50, from performing the described movement.

Alternatively, another separability of the first locking mechanism 80 from the first component 50 can be provided.

To dismantle the target apparatus 20 still further, the second component 70 can be separated from the first component 50. For this purpose, the second component 70 is pulled in a clockwise movement, relative to the views in FIGS. 1, 4 and 5, out of the first groove 57 in the first component 50. In the situations or configurations shown in FIGS. 1 to 5, the engagement of the projection 59 on the first component 50 in the groove 79 in the second component 70 and the end of the groove 79 in the second component 70 before the first end 71 of the second component 70 prevent this removal of the second component 70 from the first groove 59 in the first component 50. This no longer applies when the first locking mechanism 80 is separated or removed from the first component 50. In this case, the eccentric 83 of the pivotable structural element 81 no longer prevents the elastic portion 60 of the first component 50 from deforming radially outwards or, with respect to the views in FIGS. 1, 4 and 5, to the left and upwards. By deformation of the elastic portion 60 of the first component 50, the projection 59 on the elastic portion 60 of the first component 50 is thus able to climb out of the groove 79 in the second component 70.

The target apparatus 20 can be put together in the reverse sequence and with reverse directions of movement.

The invention being thus described, it will be obvious that the same may be varied in many ways. Such variations are not to be regarded as a departure from the spirit and scope of the invention, and all such modifications as would be obvious to one skilled in the art are to be included within the scope of the following claims.

What is claimed is:

1. A target apparatus configured to align a surgical drilling instrument, the target apparatus comprising:
   a pointer mechanism adapted to arrange at a location on a bone where a drilled hole that is to be formed is intended to emerge;
   a guide mechanism adapted to guide the surgical drilling instrument; and
   an adjustable connection mechanism with a first end that is connected to the guide mechanism, and a second end that is connected to the pointer mechanism,
   wherein the adjustable connection mechanism comprises a first component, a second component, and a locking mechanism,
   wherein the second component is movable relative to the first component along a predetermined path that is formed by a first groove in the first component, such that the second component slides within the first groove of the first component,
   wherein the first component is elastically deformable by the locking mechanism such that the second component is adapted to be locked relative to the first component by clamping.

2. The target apparatus according to claim 1, wherein the first component is elastically deformable in the area of the first groove of the first component by the locking mechanism such that the second component is adapted to be locked in the first groove of the first component by clamping.

3. The target apparatus according to claim 1, wherein the first component has an elastic portion that forms a part of an inner surface of the first groove of the first component.

4. The target apparatus according to claim 3, wherein the elastic portion of the first component is formed by a structural element that is produced separately and thereafter attached.

5. The target apparatus according to claim 3, wherein the elastic portion has a tongue-shaped design and extends along the first groove of the first component.

6. The target apparatus according to claim 3, wherein the elastic portion has two elastically deformable beam-shaped areas.

7. The target apparatus according to claim 6, wherein the two elastically deformable beam-shaped areas are formed by a first elastic web and a second elastic web that are separated by a recess.

8. The target apparatus according to claim 1, wherein the locking mechanism has an operating element that is slidable.

9. The target apparatus according to claim 8, wherein the operating element of the locking mechanism is guided in a second groove in the first component.

10. The target apparatus according to claim 9, wherein the locking mechanism further comprises an eccentric or a cam on a pivotable structural element and a lever.

11. The target apparatus according to claim 10, wherein the pivotable structural element and the lever are rigidly connected, and wherein the lever and the operating element of the locking mechanism are mechanically coupled via a connecting rod.

12. The target apparatus according to claim 1, wherein the second component has a groove in which a projection of the first component engages, and wherein the groove on the second component terminates prior to an end of the second component that is directed towards the first component such that the second component is not separatable from the first component.

13. The target apparatus according to claim 1, wherein the guide mechanism is movable relative to the first end of the adjustable connection mechanism, such that the guide mechanism is movable towards the pointer mechanism and away from the pointer mechanism, and wherein a second locking mechanism is provided, the second locking mechanism adapted to lock the guide mechanism, wherein the second locking mechanism is configured such that a movement of the guide mechanism towards the pointer mechanism is possible at all times, and wherein a movement of the guide mechanism away from the pointer mechanism is possible only upon actuation of an operating element of the second locking mechanism.

14. The target apparatus according to claim 13, wherein the second locking mechanism is configured to suppress a movement of the guide mechanism away from the pointer mechanism solely by frictional engagement.

15. The target apparatus according to claim 14, wherein the second locking mechanism comprises a lever that is pivotable about a pivot axis, a friction surface on the lever for bearing on a surface area of the guide mechanism directed away from the pivot axis, and an elastic mechanism for moving the friction surface away from the pointer mechanism, and wherein a distance of the pointer mechanism from a first plane, which is orthogonal to an axis of the guide mechanism and contains a contact point between the friction surface on the lever and the guide mechanism, is greater than a distance of the pointer mechanism from a second plane, which is orthogonal to the axis of the guide mechanism and contains the pivot axis of the lever.

* * * * *